United States Patent [19]

Codignola et al.

[11] 4,420,634

[45] Dec. 13, 1983

[54] PROCESS FOR THE OXIDATION OF UNSATURATED ALIPHATIC HYDROCARBONS

[76] Inventors: Franco Codignola, Largo Corsia dei Servi 3; Paolo Gronchi, Via Servio Tullio 4; Renato del Rosso, Via Palmanova 67; Paolo Centola, Via Paisiello 28, all of Milan, Italy

[21] Appl. No.: 214,032

[22] Filed: Dec. 8, 1980

[30] Foreign Application Priority Data

Jun. 10, 1980 [IT] Italy .................................. 22676 A/80

[51] Int. Cl.$^3$ ...................... C07C 51/25; C07C 51/09; C07C 27/12; C07C 45/32; C07C 45/34; C07C 45/35; C07C 45/37

[52] U.S. Cl. ............................. 562/512.2; 560/241.1; 560/246; 562/524; 562/544; 562/548; 562/549; 568/397; 568/398.8; 568/400; 568/469.9; 568/475

[58] Field of Search ............ 562/548, 544, 524, 512.2; 568/397, 400, 475, 398.8, 469.9; 260/413; 560/246, 241.1

[56] References Cited

U.S. PATENT DOCUMENTS

| | | | |
|---|---|---|---|
| 3,337,618 | 8/1967 | Fariss | 562/548 |
| 3,505,400 | 4/1970 | Kronig et al. | 562/524 |
| 3,875,225 | 4/1975 | Hobbs et al. | 562/524 |

FOREIGN PATENT DOCUMENTS 963430 7/1964 United Kingdom ................ 562/544

Primary Examiner—Vivian Garner
Attorney, Agent, or Firm—Cushman, Darby & Cushman

[57] ABSTRACT

The invention relates to a process for the oxidation of unsaturated hydrocarbons, particularly butenes and isobutylene, for the production of acetic acid, propionic acid and acetone. Specifically the invention comprises the highly selective oxidation of an unsaturated hydrocarbon or of a mixture of unsaturated hydrocarbons in the presence of a catalyst consisting of a complex of trivalent cobalt and of a carbonyl compound, of the aldehydic or ketonic type.

8 Claims, No Drawings

PROCESS FOR THE OXIDATION OF UNSATURATED ALIPHATIC HYDROCARBONS

The present invention relates to a process for the preparation of compounds having the following general formula:

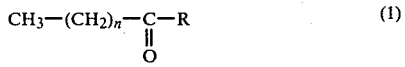
$$CH_3-(CH_2)_n-\underset{\underset{O}{\|}}{C}-R \qquad (1)$$

wherein R=H, OH, alkyl (containing 1 or 2 carbon atoms) and n=O, 1 starting from aliphatic, mono-unsaturated hydrocarbons, particularly butene-1, butene-2 and isobutylene.

In the following description, specific reference shall be made to the production of acetic acid, it having to be construed as an illustrative but non limiting sense.

BACKGROUND OF THE INVENTION

The importance of the acetic acid as a raw material for the manufacturing of several industrial products, such as esters, monomers, insecticides, metal salts etc., having a number of end uses, is well known.

In view of the importance of the acetic acid as a basic raw material, relevant research efforts have been carried out in the last twenty years, aiming to develop a more economical process for the industrial production thereof.

After the process involving the conversion of acetylene to acetic aldehyde and then the conversion of acetic acid, there has been adopted a process involving the conversion of ethylene to acetic aldehyde and then the reaction to acetic acid. The latter process, before the increase of the oil prices, has for a long time been the most economic process and still nowadays is used for a very high percentage of the worldwide production (about 35% of the U.S. production of acetic acid).

There is also known a process for the oxidation of saturated hydrocarbons, in liquid phase, called LPO; for this process n-butane is used in USA as the starting compound, whereas virgin naphtha is used in United Kingdom. To date, 40% of the U.S. production of acetic acid takes place through the latter process.

A process, already known since the beginning of this century, but developed as an industrial process only after 1960, also became of relevant importance: it is the carbonylation of methanol. The first industrial development has been achieved by BASF with a high pressure process, whereas by the Monsanto process it became possible to operate at low pressure. By the latter process 15% of the U.S. production is covered.

Owing to the development of the automotive industry and of the plastics industry, in the last ten years a novel raw material, theoretically useful for the liquid phase oxidation to acetic acid became more and more available. It is the butene fraction recovered from the crude processing in the cracking plants, for the production of gasoline, of Diesel oil and of various cuts and for the production of ethylene, propylene etc.

However, despite these large availability of by-products containing the butenes, to date no industrial process is known, according to which butenes are used for the production of acetic acid.

In fact, despite the attempts as carried out up to date, it has not yet been possible to develop a sufficiently selective process, permitting acid acetic to be produced, with high yields and in only one step, by the oxidation of butenes.

Of course, the critical point of such a development resides in the catalyst. In the past a process for the production of acetic acid by oxidation of butenes has been proposed by Bayer A. G.; such process however had no industrial outcome, since several drawbacks both from the technical and from the industrial point of view were present.

The technical drawbacks originated from the fact that a two step process was involved, according to which in the first step, by using a ion exchange resin as the catalyst and under pressure, butyl acetate was produced from acetic acid and butenes, the reaction product being separated from the unreacted compounds by complex fractionating steps.

In the second step, the butyl acetate was oxidized, under high temperature and pressure, to acetic acid; however, after a distillation step, one third (in moles) of the thus obtained acetic acid had to be recycled to the first step.

The economic drawbacks consisted in that, due to the complexity of the process, very high investment costs were involved: furthermore there was the added drawback of a low yield, (800 kg of butenes per metric ton of produced acetic acid, whereas the theoretical yield should be of 1712 kg of acetic acid per 800 kg of butenes); consequently this process is not industrially competitive with respect to the other processes.

Another process developed by Huels is known, comprising the oxidation of butenes in the vapour phase by a catalyst of vanadium and titanium oxides, the oxidation taking place at high pressure and at a temperature of between 180° and 245° C. However the yield, as acetic acid, is 46% only and a number of by-products are formed, which heavily add to the costs of the industrial operation, as in the other processes, since the separation of these by-products is necessary in order to obtain acetic acid having a commercially acceptable purity. The already mentioned LPO process would be also non competitive either with the process based on the use of ethylene as the starting compound and mainly with methanol carbonylation process.

In fact, during the oxidation, due to the rather severe reaction conditions (high pressure and temperature), a number of products, besides the acetic acid, are formed, by which the operation of the plant and particularly the fractionation step are particularly difficult and complicated.

Consequently the investment costs are very high, (for instance, in the case of the virgin naphtha 13 columns are needed) and the yield of acetic acid is not greater than 50–55%. The main purpose of the present invention is that of providing a process by which unsaturated hydrocarbons of the butene class can be used as the starting compounds, with high selectivity and yields.

DETAILED DESCRIPTION OF THE INVENTION

It has been now found and is the subject of the present invention and application that such a purpose is achieved by a process for the oxidation in only one step of mono-unsaturated aliphatic hydrocarbons, which is characterized in that the oxidation is carried out in the liquid phase, at a temperature of between 70° C. and 150° C. and at a pressure of between 5 and 50 technical atmospheres, in the presence of a catalyst consisting of a complex formed by a cobalt salt of an organic acid containing at least two carbon atoms and by a carbonyl compound of the aldehydic or ketonic type having the function of an activator.

As it will appear from the following examples, by the process of the present invention and particularly by the related catalyst, it is possible to carry out the oxidation under less severe conditions of pressure and mainly of temperature, whereby the formation of several by-products is hindered, if not prevented, the latter being responsible for the high industrial acceptance of the already known LPO process for the oxidation of saturated hydrocarbons (butane and virgin naphtha).

Another feature, important as well and wholly unexpected and unforeseeable of the process of the invention resides in that not only there are obtained high yields of conversion of the starting butenes, but the yields are furthermore increased by the conversion of part of the butanes which are unavoidably present in the starting mixture.

As regards the catalytic complex, as used in the present invention, it is formed between the trivalent cobalt ions and a carbonyl compound of the aldehyde or ketone type, particularly acetic aldehyde.

As the cobalt compounds useful for the process of the present invention, acetate, propionate, stearate and octanoate can be used, and more generally the cobalt salts of carboxylic acids containing 2 to 8 carbon atoms.

As regards the reaction solvent, the acetic acid is preferred, but other organic solvents, preferably of the protic class can be used. The catalyst complex per se is already known in the literature and has been industrially used in the oxidation of mono- and di-substituted alkylbenzenes and cyclohexane, but not even suggested as regards its use in the oxidation of butenes to obtain the compounds of the present invention.

It is further important to point out that the process of the present invention does find identical use, not only in the production of acetic acid, but also in that of the propionic acid and of acetone, these products being very important from the industrial point of view.

Of course, by controlling the composition of the starting mixture, it is possible to control, both qualitatively and quantitatively, the composition of the resulting mixture.

The following non-limiting examples illustrate the invention.

EXAMPLE 1

An autoclave of about 4 liter capacity, having a variable speed stirrer (0 to 2500 r.p.m.) an automatically adjustable heating oven, a gas inlet and outlet, a siphoning diving pipe, an internal cooling coil, and a safety valve, is charged at room temperature with 1,078 g of acetic acid, 27 g of acetic aldehyde, 25 g of water, 80 g of $Co(CH_3COO)_2 \cdot 4H_2O$, and a mixture comprising 108 g of butene-2 cis and 110 g of butene-2 trans, the mixture being stirring at 850 r.m.p.

The autoclave pressure, the stirring being continued, is brought to 35 technical atmospheres by compressed air and the heating is started in order to bring the temperature to 90° C.

Before reaching such a temperature, the absorption of oxygen is observed, and the colour of the reaction mixture changes from red to dark emerald green, which is the sign of the fact that the catalytic complex comprising the cobalt salt and the carbonyl compound has been formed. Once the temperature of 90° C. is attained, the reaction is conducted, the temperature being maintained at 90° C. and the pressure at the same value, the latter being maintained by continuous make up of pure oxygen for two hours more. Once the reaction is completed, the autoclave is cooled together with the contents thereof to room temperature. During the two hours of reaction, a sample of the reaction mixture is taken every 30 minutes, in order to control that the catalytic complex of dark emerald green colour remains unchanged; in the case in which the reaction mixture changes to pink colour, 5 to 10 g of acetic aldehyde are added to the autoclave.

At this point, by means of the gas outlet tap, the content of the autoclave is expanded and the gas stream is passed through several coolers at decreasing temperatures and lastly in a liquid air trap. Once the expansion is completed, the reaction mixture remaining in the autoclave and the liquid and gaseous fractions obtained from the expanding gaseous stream are analyzed by gaschromatographic methods. The following results are obtained:

Converted butenes: 86.7% (189 g).

There are thus obtained 155 g of acetic acid and 165.6 g of a mixture of mono-acetate and diacetate of butane-2,3-glycol.

The latter products, which are probable intermediates of the oxidation reaction, are recovered by distillation and are further oxidized under the same conditions as previously illustrated.

These products are totally and wholly oxidized to acetic acid, thus giving further 224 g of acetic acid, with a total yield of acetic acid of 379 g, corresponding to about 94% of the theoretical yield.

EXAMPLE 2

In a tubular reactor, comprising several bladed turbines to ensure a complete distribution of the oxidizing air in the liquid mixture and having 50 mm diameter and 60 cm height, 125 g/h of a mixture are fed by parallel current flow and from the bottom of the reactor, the mixture containing by weight 89% of acetic acid, 2.2% of acetic aldehyde, 2.1% of water and 6.7% of colbaltous acetate tetrahydrate. The temperature is maintained at 90° C. and from the bottom there are fed in parallel current flow 110 g of the same mixture of butene-2 cis and butene-2 trans of example 1 and a stream of atmospheric air, under a pressure of 35 technical atmospheres. At the outlet of the reactor, the expansion of the mixture takes place and both the liquid and the gaseous streams are analyzed according to known methods.

As a matter of fact, the total conversion of the butenes is achieved, with a yield slightly higher than 94–95% of the theoretical value.

EXAMPLE 3

Under the same conditions as in the example 1, 180 g of a mixture of $C_4$ hydrocarbons, exhausted of butadiene and isobutylene and containing 11.7% of butene-2 cis and butene-2 trans are charged.

The reaction and the treatment of the mixture obtained at the end of the reaction are carried out as disclosed in the example 1.

The butenes-2 present in the mixture was completely oxidized to acetic acid and the yield with respect to the theoretical value is slightly higher than 100%, due to the oxidation of the butanes; the latter oxidation is probably due to a subtraction of hydrogen from the molecule of the saturated butanes due to the radicals present in the oxidizing solution.

EXAMPLE 4

In the same autoclave of the example 1, 285 g of 99% pure cold butene-1 are charged together with a catalytic mixture comprising acetic acid (1,049 g), acetic aldehyde (27 g), water (25 g) and Co(CH$_3$COO)$_2$.4H$_2$O (80 g).

The reaction is carried out as in the example 1 with the same chemical pattern. The final analysis of the reaction mixture, as effected by the same gas-chromatographic method, indicates that 72 g of propionic acid have been obtained, together with about 83 g of a mixture of mono-acetate and di-acetate of butane-1,2-glycol. The latter mixture is further oxidized, after the separation, as disclosed in the example 1, and further 51 g of propionic acid are obtained whereby the total amount of propionic acid is 123 g with a selectivity of 52%.

EXAMPLE 5

Under the same operating conditions of the example 1 and using the same catalytic mixture, 232 of 99% pure cold isobutene are charged in the autoclave.

The reaction takes place according to the same characteristics as described in the examples 1, 3 and 4. Once the reaction is completed, both the recovered gases and the final reaction mixture are analyzed. The gas-chromatographic analysis shows the presence of acetone (123 g) and of a mixture of acetates of isobutylene glycol.

The latter, after separation from the final reaction mixture and oxidation under the identical reaction conditions, gives further 18 g of acetone. There is thus obtained a total yield of the oxidation reaction of isobutene to acetone of 61% with a selectivity of 91%.

EXAMPLE 6

In the same tubular reactor and under the same conditions disclosed in the examples 2 and 5, pure isobutene is reacted with the catalytic mixture of the example 2. After the expansion, the analysis of the gases and of the reaction mixture shows that a selectivity of about 93–94% has been achieved in the oxidation reaction of isobutene to acetone.

It is to be pointed out that, in the catalyst used in the process of the present invention, the presence of other ions, such as for instance manganese, having like oxidizing function, cannot be excluded.

We claim:

1. A process for the selective oxidation in liquid phase of mono-unsaturated aliphatic hydrocarbons to obtain compounds having the formula:

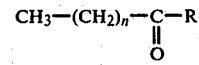

wherein: R=H, OH or C$_1$–C$_2$ alkyl and n=O or 1, wherein the oxidation is conducted in the presence of oxygen or air, in an organic solvent, at a temperature of 70° to 150° C. and at a pressure of 5 to 50 atmospheres, in the presence of a catalyst consisting of a trivalent cobalt complex formed by a cobalt salt of an organic acid containing at least two carbon atoms with a carbonyl compound of the aldehyde or ketone type.

2. A process according to claim 1 wherein said unsaturated aliphatic hydrocarbon is a mixture of butene-2 cis and butene-2 trans.

3. A process according to claim 2 wherein mono-acetate and di-acetate of butane-2,3-glycol are obtained as by-products of the reaction, said by-products, after separation, being oxidized under the same reaction conditions as in claim 1 to form acetic acid.

4. A process according to claim 1 wherein said unsaturated aliphatic hydrocarbon is isobutylene, and there is obtained acetone together with acetates of isobutylene-glycol as by-products which acetates after a separation step, are further oxidized to acetone under the same reaction conditions as in claim 1.

5. A process according to claim 1 wherein the organic solvent is acetic acid and said carbonyl compound is acetic aldehyde.

6. A process according to claim 1 or 5 wherein said unsaturated aliphatic hydrocarbon is butene-1 and there is obtained propionic acid, together with mono-acetate and di-acetate of butane-1,2-glycol as by products, which acetates, after a separation step, are further oxidized to propionic acid under the same reaction conditions as in claim 1.

7. A process according to claim 1 or 5 wherein said cobalt salt is a cobalt salt of a carboxylic acid containing 2 to 8 carbon atoms.

8. A process for the selective oxidation in the liquid phase of a mono-saturated aliphatic hydrocarbon or a mixture of said mono-unsaturated aliphatic hydrocarbons to produce a compound of the formula:

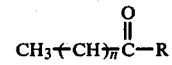

where R is H, —OH or C$_1$–C$_2$ alkyl and n is zero or one, wherein said oxidation is conducted in the presence of oxygen, in acetic acid as solvent, at a temperature of about 70° to about 150° C. and at a pressure of about 5 to about 50 atmospheres and in the presence of a catalyst consisting of a trivalent cobalt complex formed by a cobalt salt of a C$_2$–C$_8$ carboxylic acid with an aldehyde or ketone carbonyl compound.

* * * * *